(12) United States Patent
Clinton-Barnett

(10) Patent No.: US 8,758,276 B2
(45) Date of Patent: Jun. 24, 2014

(54) PATIENT ASSESSMENT APPARATUS AND METHOD

(76) Inventor: Nathan R. Clinton-Barnett, Oxford, MI (US)

( * ) Notice: Subject to any disclaimer, the term of this patent is extended or adjusted under 35 U.S.C. 154(b) by 384 days.

(21) Appl. No.: 13/303,431

(22) Filed: Nov. 23, 2011

(65) Prior Publication Data

US 2013/0131553 A1  May 23, 2013

(51) Int. Cl.
*A61B 5/117* (2006.01)
*A61B 5/103* (2006.01)

(52) U.S. Cl.
USPC .......................................................... 600/595

(58) Field of Classification Search
USPC ........... 600/595; 223/94, 1, DIG. 4; 24/598.1, 24/601.6, 716; 33/471, 512, 1 N
See application file for complete search history.

(56) References Cited

U.S. PATENT DOCUMENTS

| | | | |
|---|---|---|---|
| 1,743,234 A * | 1/1930 | Porter | 223/94 |
| 6,256,532 B1 | 7/2001 | Cha | |
| 6,662,388 B2 | 12/2003 | Friel et al. | |
| 7,163,516 B1 | 1/2007 | Pagnacco et al. | |
| 7,526,071 B2 | 4/2009 | Drapeau | |
| 7,556,045 B1 | 7/2009 | Recknor et al. | |
| 8,341,850 B2 * | 1/2013 | Merchant | 33/471 |
| 2005/0159675 A1 | 7/2005 | Harbin et al. | |
| 2007/0108357 A1 | 5/2007 | Plowman | |

OTHER PUBLICATIONS

New BioSway: Lightweight, Portable Balance Assessment and Training, www.biodex.com/biosway, Nov. 2010.
Dynavision D2: Greater Function, Greater Freedom—A Phone Call Away, Bioness, Inc., www.bioness.com, Apr. 23, 2010.
Therapytimes, A New Vision of Rehabilitation: Recovering Cognitive Abilities with Dynavision, Jun. 15, 2010.
A. A. Ahmed et al., On Use of a Nominal Internal Model to Detect a Loss of Balance in a Maximal Forward Reach, J. Neurophysiol 97:2439-2447, 2007.

* cited by examiner

*Primary Examiner* — Brian Szmal
(74) *Attorney, Agent, or Firm* — Brooks Kushman P.C.

(57) ABSTRACT

A patient assessment apparatus, such as for balance assessment, includes an elongated member having a length and first, second and third positions along the length, a first receiving member situated at the first position, and a second receiving member situated at the third position, the second position situated between the first and third positions. The first and second receiving members are each arranged to receive a marker from a patient. Reach characteristic data is collected from a patient using the balance assessment apparatus, and the reach characteristic data is analyzed to determine whether the patient has a balance deficit.

18 Claims, 3 Drawing Sheets

Ascending: _____/48                    Reaching: _____/64                    Balance Arc: _____/36

Distance of Apparatus              Distance of Apparatus              Distance of Apparatus
    □ 3 inches                         □ 3 inches                         □ 3 inches

| A - Horizontal | |
|---|---|
| Left Hand – A B C D | |
| Left Hand – D C B A | |
| Right Hand – D C B A | |
| Right Hand – A B C D | |
| SCORE | /16 |

| D - Right Side Away 15° | |
|---|---|
| Right Hand – A B C D | |
| Right Hand – D C B A | |
| Left Hand – A B C D | |
| Left Hand – D C B A | |
| SCORE | /16 |

| H - Vertical | |
|---|---|
| Right Hand – Right to Left | |
| Right Hand – Left to Right | |
| Left Hand – Left to Right | |
| Left Hand – Right to Left | |
| SCORE | /12 |

| B - Ascending Right to Left 45° | |
|---|---|
| Left Hand – D C B A | |
| Left Hand – A B C D | |
| Right Hand – D C B A | |
| Right Hand – A B C D | |
| SCORE | /16 |

| E - Left Side Away 15° | |
|---|---|
| Left Hand – D C B A | |
| Left Hand – A B C D | |
| Right Hand – D C B A | |
| Right Hand – A B C D | |
| SCORE | /16 |

| I - Toward 30° | |
|---|---|
| Right Hand – Right to Left | |
| Right Hand – Left to Right | |
| Left Hand – Left to Right | |
| Left Hand – Right to Left | |
| SCORE | /12 |

| C - Ascending Left to Right 45° | |
|---|---|
| Right Hand – A B C D | |
| Right Hand – D C B A | |
| Left Hand – A B C D | |
| Left Hand – D C B A | |
| SCORE | /16 |

| F - Right Side Away 45° | |
|---|---|
| Right Hand – A B C D | |
| Right Hand – D C B A | |
| Left Hand – A B C D | |
| Left Hand – D C B A | |
| SCORE | /16 |

| J - Away 30° | |
|---|---|
| Right Hand – Right to Left | |
| Right Hand – Left to Right | |
| Left Hand – Left to Right | |
| Left Hand – Right to Left | |
| SCORE | /12 |

| G - Left Side Away 45° | |
|---|---|
| Left Hand – D C B A | |
| Left Hand – A B C D | |
| Right Hand – D C B A | |
| Right Hand – A B C D | |
| SCORE | /16 |

Assessment Score Total: _____/148

FIGURE 5

PATIENT ASSESSMENT APPARATUS AND METHOD

TECHNICAL FIELD

Embodiments relate to an apparatus and method for patient assessment, such as balance assessment.

BACKGROUND

Accidental falls are the second leading cause of death worldwide. In the United States alone, they accounted for 19,656 deaths in the year 2005 (World Health Organization, 2006). Non-fatal falls have many adverse side effects, including high medical expenses related to hospitalizations and subsequent therapy, as well as decreased quality of life. According to the Center for Disease Control (CDC) (2010), the cost of fatal falls in the U.S. in 2000 totaled 179 million dollars, while non-fatal falls cost an additional 19 billion dollars. Declines in quality of life can result from a loss of independence resulting from diminished mobility, physical fitness and levels of activity that may occur after a fall. These costs, as well as the number of individuals experiencing falls are predicted to increase, as the baby boomer generation approaches older adulthood. For these reasons, falls have been considered a major health concern in the United States, and are only anticipated to increase in frequency.

Prior research (Oddsson et al., *European Review of Aging and Physical Activity*, 4: 15-23. 2007; Talbot et al., *BMC Public Health*, 5:86, 2005) has identified declines in balance as a leading factor contributing to falls. Balance may be defined as the " . . . ability to maintain a functional posture through motor actions that distribute weight evenly around the body's center of gravity" (Jacobs and Jacobs, *Quick Reference Dictionary for Occupational Therapy*, p. 23, 2009). Not only is balance essential for the prevention of falls, but a deficit in balance can impact an individual's ability to perform activities of daily living (ADL) (Blum and Korner-Bitensky, *Physical Therapy*, 88(5): 559-566, 2008). Therefore, it may be important to identify balance deficits displayed by an individual because of the negative impact they may have on the individuals' overall function.

There are many balance assessment tools currently utilized in clinical practice that detect the presence of balance deficits and evaluate the effectiveness of treatment interventions. The Berg Balance Scale (BBS) has been described as the "gold standard" in measuring functional balance performance. The BBS assesses gross motor reaching movement patterns and provides a numerical assessment of a person's balance performance during a series of increasingly more complex functional movements (Blum and Korner-Bitensky, 2008; Smith et al., *Clinical Rehabilitation*, 18: 811-818, 2004). The Falls Efficacy Scale International (FES-I) is a survey questionnaire that assesses an individual's degree of concern about falling while performing ADLs. (Delbaere et al., *Age and Ageing*, 39: 210-216, 2010; Hotchkiss et al., *American Journal of Occupational Therapy*, 58: 100-103, 2004; Trader et al., *Journal of Geriatric Physical Therapy*, 26(3): 3-8, 2003). The Tinetti Balance Assessment Tool measures both static and dynamic balance during functional tasks that emphasize stability. Scores are assigned based on the amount of assistance the client requires during completion of specific task criteria (Sterke et al., *Intergenerational Psychogeriatrics*, 22(2): 254-263, 2010). The Multi-Directional Reach Test (MDRT) is an assessment used to measure an individual's anterior, posterior, right and left functional reaching limits (Winser and Kannan, *Global Journal of Health Science*, 3(1): 90-97, 2011).

However, there are several limitations among the most commonly used balance assessment tools. A significant limitation present in several of these assessments is that they do not examine balance while reaching and performing trunk rotation, which are both crucial elements of performing everyday tasks (Holein-Jenny et al., *Ergonomics*, 50(5), 2005; Smith et al., 2004; Sterke et al., 2010; Winser and Kannan, 2011). In addition, several of these tests do not identify the specific point at which the participant experiences a balance deficit during the completion of task specific patterns (Smith et al., 2004; Sterke et al., 2010). A lack of this knowledge could prevent clinicians from designing an intervention that appropriately addresses the individual's deficits in balance.

Additionally, fine motor abilities in cooperation with gross motor reaching tasks are not measured in commonly used balance assessments (Holbein-Jenny et al., 2005; Winser and Kannan, 2011). Subjectivity of the data collected in the FES-I can reduce the reliability of assessment scores, due to individual interpretations of survey questions and participants' perceived abilities (Hotchkiss et al., *American Journal of Occupational Therapy*, 58: 100-103, 2004; Trader et al., 2003). Finally, the BBS includes common household objects that have physical characteristics which may vary between administered tests, and may reduce reliability due to inconsistencies in instrumentation (Smith et al., 2004). The limitations in current balance assessments illustrate the need for a tool that more comprehensively addresses balance issues and relates them to functional outcomes.

SUMMARY

In an embodiment, a patient assessment apparatus includes an elongated member having a length and first, second and third positions along the length, a first receiving member situated at the first position, and a second receiving member situated at the third position, the second position situated between the first and third positions, the first and second receiving members each for receiving a marker from a patient for use in patient assessment.

In another embodiment, a patient assessment apparatus includes an elongated member having a length and first, second and third positions along the length, a first receiving member situated at the first position, and a second receiving member situated at the third position, the second position situated between the first and third positions, the first and second receiving members each for receiving a marker from a patient for use in patient assessment. A primary pivot connector is situated at the second position, wherein the elongated member includes a first extending portion and a second extending portion extending from and rotatable about the primary pivot connector. A support member extends from the primary pivot connector and supports the elongated member, wherein at least one of the elongated member and the support member are segmented so as to be modular for assembly and disassembly of the apparatus.

In one embodiment, a method of assessing patient balance includes receiving reach characteristic data collected from a patient using a balance assessment apparatus, the apparatus including an elongated member having a length and first, second and third positions along the length, a first receiving member situated at the first position, and a second receiving member situated at the third position, the second position situated between the first and third positions, wherein the first and second receiving members are each for receiving a marker from a patient. The method further includes analyzing the reach characteristic data to determine whether the patient has a balance deficit.

BRIEF DESCRIPTION OF THE DRAWINGS

FIG. 5 shows an assessment score sheet according to an embodiment.

DETAILED DESCRIPTION

Figure 1:
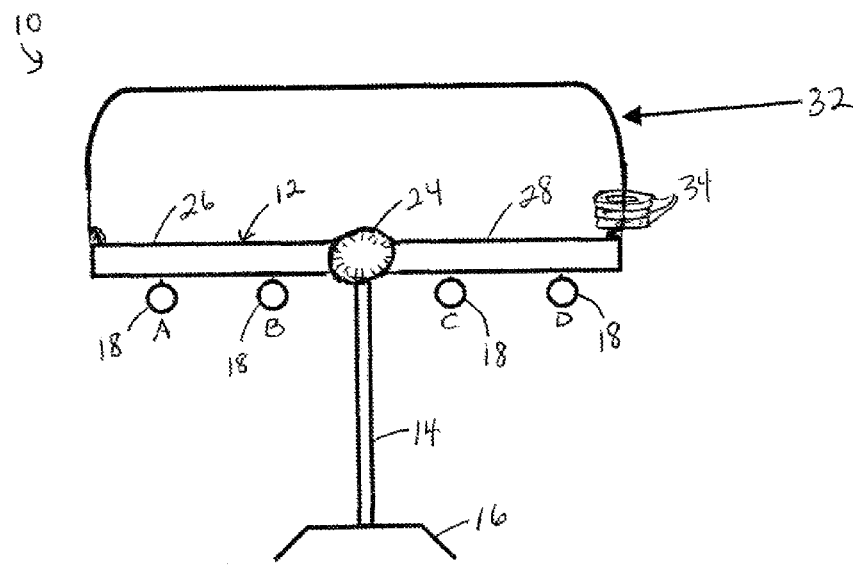
FIG. 1 is a front elevational view of an assessment apparatus according to an embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The patient assessment apparatus and method according to embodiments described herein may be used to quantitatively measure a patient's ability to maintain balance during various weight shifts in a specified pattern. The assessment may include three sections that can be given consecutively or separately, depending upon the patient's needs and the situation. According to one embodiment, a numerical score is given in each section, allowing for the patient's progress to be tracked over time. During the assessment, the patient may remain flat footed on the ground and initiate movement within the frontal plane, simulating functional use of the upper extremity. A fine motor component may also be incorporated in the assessment that requires the patient to place an object at a specified location on the apparatus.

In comparison with previous assessment methods, the method described herein uses one standardized apparatus, as opposed to multiple items used in other assessments, providing consistency across each test administered. The assessment method examines the specific point at which a balance dysfunction occurs during the completion of a task, as well as a patient's balance while reaching and performing trunk rotation. Knowing the specific point where balance dysfunction occurs and having the patient initiate trunk rotation while reaching allows an administrator to determine whether or not the patient experiences a balance deficit on a specific side of his/her body, and if dysfunction will also be present in gait. Additionally, through the fine motor component of the assessment method, the administrator can discern if the patient is having difficulties with balance during gross motor movements and/or while initiating fine motor coordination.

More particularly, the assessment method includes an individually administered, standardized assessment used to evaluate a patient's ability to maintain balance through specific weight-shifting patterns while using fine motor skills to place markers on specific receiving members, or to move objects through a pre-set plane. In one embodiment, the patient engages an assessment apparatus while following a specific and ordered protocol. The assessment method measures the patient's ability to maintain balance while moving through various weight shifting patterns (e.g., outward/inward reach, upward/downward reach, with or without trunk rotation, etc.) while using fine motor skills to place markers on specified receiving members. These weight shifting patterns, combined with fine motor precision and trunk rotation, simulate the various bodily positions and actions associated with the performance of ADL.

The patient assessment apparatus and method allow the assessment of balance in individuals in a variety of age groups and with a variety of medical conditions, and may be used for all areas which require the measurement and evaluation of a patient's balance ability, and also for treatment and therapy. These areas can include, but are not limited to, healthcare settings, such as hospitals and therapy clinics, work hardening/functional return clinics, assisted living and nursing homes, etc.

An assessment apparatus according to one embodiment is depicted in FIG. 1 and designated generally with reference numeral 10. The apparatus 10 includes an elongated member or bar 12 attached to a support member or pole 14 for supporting the bar 12 on a surface, and may be attached to a stand 16. The bar 12 is depicted as being generally rectangular, but could have any suitable shape or cross-section. In one embodiment, the bar 12 may be about 48 in. in length, but is not limited thereto. In addition, the length of the bar 12 can be adjustable, such as via a telescoping arrangement, and thus extended or shortened to customize or vary the difficulty of the assessment.

Figure 2:
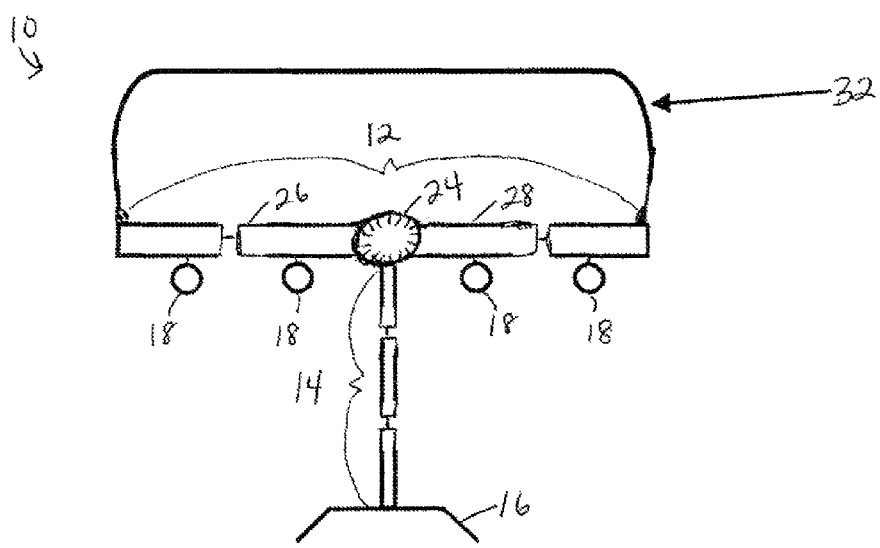
FIG. 2 is a front elevational view of an assessment apparatus according to an embodiment, wherein the apparatus is modular.

In one embodiment, the length of the pole 14 is also adjustable, such as via telescoping, such that the pole 14 may be adjusted to allow the height of the bar 12 to be, for example, but not limited to, between about 48 in. and 61 in. This range includes the bottom $5^{th}$ percentile for female shoulder height, and the $95^{th}$ percentile for male shoulder height. In another embodiment, the pole 14 and/or stand 16 could be shortened in order to use the apparatus 10 as a table-top activity. Alternatively, the bar 12 could be mounted to the wall, such as via the pole 14 or other support member, and positioned accordingly to complete the assessment. As shown in FIG. 2, in one embodiment, the bar 12 and/or pole 14 portions of the apparatus 10 could be modular and segmented into different units, providing the flexibility to select only certain units for assembly as well as facilitating storage and transportability.

Figure 4:
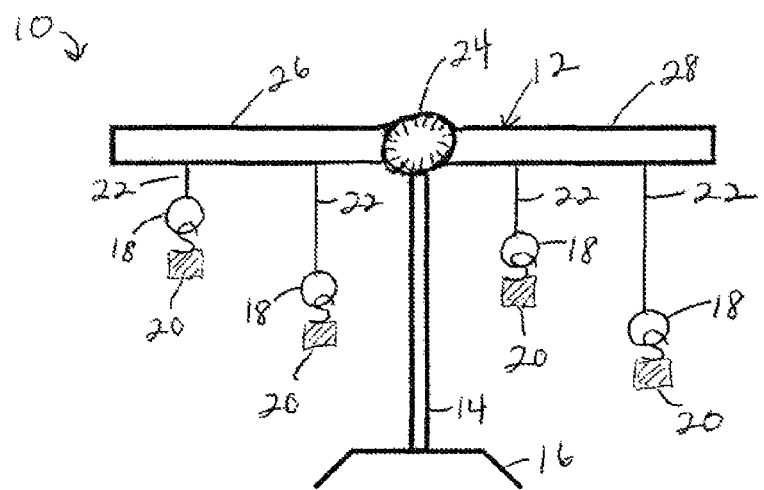
FIG. 4 is a front elevational view of an assessment apparatus according to an embodiment, wherein the apparatus includes receiving members disposed at varying distances from the elongated member.

The bar 12 includes receiving members 18 such as, but not limited to, eyelets attached thereto for receiving markers 20 (see FIG. 4) as described in more detail below. The receiving members 18 may be designated A, B, C, and D from left to right as shown in FIG. 1. In one embodiment, the receiving members 18 may be positioned below the bar 12 as shown. With reference to FIG. 4, the receiving members 18 can also be positioned at varying distances below or distanced from the bar 12, such that the receiving members 18 lie along different horizontal axes from each other and with respect to a longitudinal axis of the elongated member 12. The receiving members 18 can be attached to the bar 12 with extension members 22 so as to be at a fixed distance therefrom or adjustable, such as via a telescoping arrangement, in order to customize or vary the difficulty of the assessment.

In one embodiment, the bar 12 is attached to the pole 14 via a hinge or primary pivot connector 24 such that bar 12 is rotatable about the primary pivot connector 24 in a substantially frontal or vertical plane. The primary pivot connector 24 may allow for discrete increments (e.g., every 2 degrees) of rotation of the bar 12 thereabout where the bar 12 can be held at a certain position, allow rotation within a set angular boundary (e.g., 0-180 degrees), and/or allow complete rotation of 360 degrees about the primary pivot connector 24. The bar 12 may also be rotatable in a substantially transverse or horizontal plane, such that the primary pivot connector 24 would be a universal joint, again allowing for discrete increments (e.g., every 2 degrees) of rotation of the bar 12 thereabout where the bar 12 can be held at a certain position, allow rotation within a set angular boundary (e.g., 0-180 degrees), and/or allow complete rotation of 360 degrees about the primary pivot connector 24.

In one embodiment, the B position receiving member 18 is situated at a first position along the length of the elongated member 12, the primary pivot connector 24 is situated at a second position along the length of the elongated member 12, and the C position receiving member 18 is situated at a third position along the length of the elongated member 12. The first and third positions may be equidistant from the second position. Furthermore, the A position receiving member 18 is situated at a fourth position along the length of the elongated member 12, and the D position receiving member 18 is situated at a fifth position along the length of the elongated member 12, wherein the fourth and fifth positions may be equidistant from the second position. For example, the first and third positions may each be spaced about 10 in. apart from the second position. With this spacing, the distance between the first and third positions would be about 20 in. apart, reflecting the average shoulder breadth of the U.S. male based on anthropometric data. With the fourth and fifth positions an additional 10 in. away from the first and third positions, respectively, this exemplary spacing simulates a half shoulder-breadth length outside of the normal breadth. Of course, different receiving member 18 locations and spacing distances are also contemplated.

Figure 3:
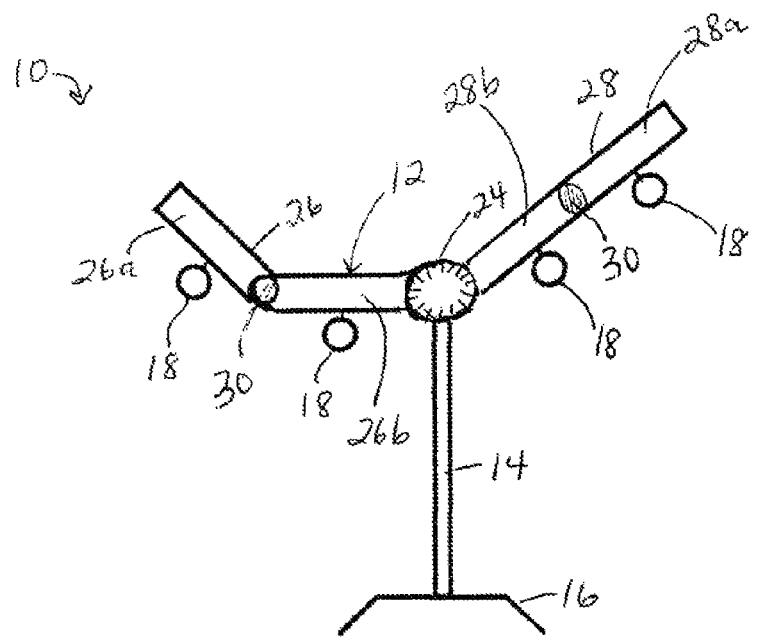
FIG. 3 is a front elevational view of an assessment apparatus according an embodiment, wherein the apparatus includes rotatable portions.

In the embodiment depicted in FIG. 3, bar 12 has a first extending portion 26 and a second extending portion 28 connected to the primary pivot connector 24 on opposite sides thereof. The first and second extending portions 26, 28 can be rotatable about the primary pivot connector 24, or independently rotatable about the primary pivot connector 24 as shown. In addition, hinges or secondary pivot connectors 30 can be provided on one or both extending portions 26, 28, such that each portion 26, 28 is further divided into sub-portions 26a, 26b and 28a, 28b which are also independently rotatable to customize and change the angle of reach for the receiving members 18. Both the primary and secondary pivot connectors 24, 30 may include indicia of angular rotation for indication a rotation angle of the extending portions 26, 28 and sub-portions 26a,b and 28a,b.

Apparatus 10 may also include an arc member 32 attached to the bar 12, such as at or near the ends thereof as shown in FIGS. 1 and 2. In one embodiment, the length of the arc member 32 is about 53 in., but is not limited thereto. The arc member 32 may be rotatably attached to the bar 12, for example, providing positions such as, but not limited to, 30 degrees away from the patient, 30 degrees toward the patient, and positions in between. The arc member 32 can be varying in length and/or design (e.g., U-shaped, V-shaped, etc.) to customize or change the difficulty of the assessment. Objects 34 such as, but not limited to, rings may be slidably disposed on the arc member 32 as shown in FIG. 1 for movement therealong as described below.

The markers 20 may have any configuration suitable for grasping by the patient and placing on the apparatus 10, and are not limited to the exemplary shape and size illustrated in FIG. 4. In one embodiment, the markers 20 may be generally flat such that multiple markers 20 are easily held in one of the patient's hands. The markers 20 may include S-hooks or the like to hang on the receiving members 18, although engagement between the markers 20 and the receiving members 18 is not limited to this configuration. For example, magnetic and fabric (e.g., VELCRO®) type interfaces between the markers 20 and receiving members 18 are also contemplated. The components of apparatus 10 can be constructed from any suitable material, such as metal or plastic, and can be disassembled for storage.

The assessment method may determine the balance capabilities of a patient, wherein balance may be defined as maintaining a state of equilibrium of the body. These capabilities are assessed through reach characteristic data obtained by the patient executing various actions of placing the markers 20 on the receiving members 18 or moving the objects 32 along the arc member 30. In one embodiment, balance must be maintained while placing the markers 20 on the receiving members 18 in order to score a point. Standing neutral is defined as the patient placing his/her feet shoulder-width apart with the upper body/trunk positioned vertical from the stance. The patient's shoulders are vertically aligned with his/her hips to provide a strong base of support during weight shifting maneuvers. Step is defined as the patient moving either foot or both feet in a supportive fashion during the act of placing a marker 20 on the receiving member 18 and is considered a loss of balance in accordance with one embodiment of the assessment method. A step includes, but is not limited to, removing the foot from the ground and placing it in another location, sliding the foot from its original location to another, etc. A step does not include pivoting on the ball of the foot while shifting weight, lifting the heel of the foot off the ground while the ball of the foot maintains its original position. A step cannot occur when the patient is not in the act of placing a marker 20 on an assigned receiving member 18, however the patient must return to standing neutral before placing the next marker 20.

Balance is considered maintained if the patient's upper body exhibits a delay in returning to standing neutral but does so without outside assistance (grabbing the apparatus 10, having the administrator aid the patient, etc.), or making a step to remain in equilibrium. Any upper body action (arm movements, etc.) to maintain balance are considered within the realm of control unless lower extremity movement occurs and will not be considered a loss of balance.

In order to begin the assessment, the patient will be positioned away from all walls and with enough room to move without impedance from objects or barriers. In one embodiment, the patient will stand at standing neutral on a flat surface while the administrator marks their place by either drawing a line or placing a strip of tape in front of the patient's feet on the floor, with the ends of the patient's feet aligned with the back edge of the marked line/tape. This line/foot placement should be maintained throughout the assessment while in standing neutral and engaging in the assessment.

In one embodiment, to set up the apparatus 10, the patient may be asked to extend his/her arms directly in front of their body and parallel to the floor, and then the apparatus 10 will be placed in front of the patient's hands. The support member 14 may then be adjusted so that the bar 12 is even with the tips of the patient's middle fingers. In one embodiment, the distance from the tip of the patient's middle digit to the arm 12 is selected to be 3 inches, although other distances are also possible.

The patient's arms should be straight with no bending at the elbows, wrist, or fingers, and the middle fingers of both hands should be even with one another. The patient's shoulders should be vertical to the patient's hips with the back straight, with no rolling of the shoulders or hunching over, if possible. If the condition of the patient does not allow for this positioning, notation should be made before the patient begins the assessment. This posturing will not necessarily exclude the patient from participating in the assessment.

In one embodiment, the administrator may place a gait belt around the patient as a safety precaution, with either the administrator or another trained professional available for standby assistance. The administrator should not allow the presence of the gait belt to interfere with the patient's movement patterns and should not hold the gait belt unless the administrator feels it is necessary.

With reference to FIG. 5, the assessment method may include three separate test batteries: ascending, reaching, and balance arc. These test batteries can be completed together to create a total balance assessment, or individually to evaluate and track scores of in a specific area. Each test battery includes several positions (e.g., horizontal, ascending from left to right at 45 degrees, left side away at 15 degrees, etc.). Each position includes several actions (e.g., left hand ABCD, right hand DCBA, etc.). For each position, the administrator will adjust the positioning of the apparatus 10 to replicate the position named in that section. Each placement will have a set setting in order to ensure continuity in the assessment.

In one embodiment, four measurements may be used for each of the ascending and reaching tasks, which requires the patient to move from one shoulder width to the other. As described above, positions A and D may be set at two shoulder widths from the center of the body, while positions B and C may be set to be in front of the patient's left and right shoulders, respectively. The distance between the receiving members 18 causes the patient's body to rotate at the trunk and reach outside the shoulder width. In one embodiment, three measurements may be used for each of the balance arc tasks. Of course, other numbers of measurements can also be utilized.

In the ascending battery, the bar 12 is rotated away from a starting position (e.g., FIG. 1), within the frontal/vertical plane and set at various testing positions. In the reaching battery, the bar 12 is rotated away from the starting position within the horizontal/transverse plane and set at various testing positions. For the ascending and reaching batteries, the patient may have all the markers 20 in his/her hand which is not in use. In one embodiment, the patient will begin standing neutral, place the marker 20 at an instructed receiving member 18, then return to standing neutral before placing the subsequent marker 20, moving from left to right, or right to left as indicated. This is to ensure that there is a gradual weight shift from one side to the next, limiting the resetting of balance. Once all four markers 20 (or lesser number if the patient fails to achieve a score of 4) have been placed, the administrator will remove the markers 20 and hand them back to the patient.

The objects 34 will be stationary when not in use on the arc member 32. In one embodiment, the patient will begin in standing neutral before grasping an object 34 and sliding it along the arc member 32. He/she will then return to standing neutral before attempting the second and third objects 34.

An example of an assessment score sheet is illustrated in FIG. 5. In one embodiment, each marker 20 that is successfully placed during each action in the ascending and reaching batteries will be scored 1 point in the corresponding box, with a minimum of 0 points and a maximum of 4 points awarded.

Each object 34 successfully moved along the arc member 32 in its entirety in the balance arc battery will be awarded 1 point in the corresponding box, with a minimum of 0 points and a maximum of 3 points awarded.

In one embodiment, the patient will get two opportunities to hang all four markers 20 or move all three objects 32 along the arc member 32. The administrator tallies up the scores from the boxes for each trial, counting only the second trials if two were performed, and records the total score for the section in the corresponding box at the bottom of each position section. The scores of each position section in a battery are added together and recorded at the top of the assessment score sheet in each respective battery category. The battery scores recorded at the top of the assessment score sheet are then added together to obtain an overall score of the assessment method.

Low scores assessments indicated with reference numeral 40 may indicate imbalance on the patient's right side. Low scores in assessments indicated with reference numeral 42 may indicate imbalance on the patient's left side. Low scores in assessments indicated with reference numeral 44 may indicate imbalance when the patient shifts weight from the right to left side. Low scores in assessments indicated with reference numeral 46 may indicate imbalance when the patient shifts weight from the left to right side. Low scores in the ascending battery may indicate imbalance when shifting weight upward in stance. Low scores in the reaching battery may indicate imbalance when shifting weight outward in stance. Low scores in the balance arc battery may indicate imbalance during trunk rotation.

Therefore, the patient assessment method and apparatus described herein allow for the determination of the specific point at which a balance dysfunction occurs during the completion of a task, as well as an individual's balance while reaching and performing trunk rotation. This information allows an administrator to determine whether or not the patient experiences a balance deficit on a specific side of their body, imbalance during specific weight shifts, and imbalance during trunk rotation, as well as whether balance difficulties are manifested during gross motor movements and/or while initiating fine motor coordination.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A patient assessment apparatus, comprising:
an elongated member having a length and first, second and third positions along the length;
an arc member attached to the elongated member;
a first receiving member situated at the first position; and
a second receiving member situated at the third position, the second position situated between the first and third positions, the first and second receiving members each for receiving a marker from a patient for use in patient assessment.

2. The patient assessment apparatus of claim 1, further comprising a primary pivot connector situated at the second position, and the elongated member including a first extending portion and a second extending portion connected to and extending from the primary pivot connector.

3. The patient assessment apparatus of claim 2, further comprising a support member extending from the primary pivot connector and supporting the elongated member.

4. The patient assessment apparatus of claim 3, wherein at least one of the elongated member and the support member is segmented so as to be modular for assembly and disassembly of the apparatus.

5. The patient assessment apparatus of claim 2, wherein each of the first and second extending portions is rotatable about the primary pivot connector.

6. The patient assessment apparatus of claim 5, wherein each of the first and second extending portions is independently rotatable about the primary pivot connector.

7. The patient assessment apparatus of claim 5, wherein the elongated member is rotatable in a vertical plane.

8. The patient assessment apparatus of claim 5, wherein the elongated member is rotatable in a horizontal plane.

9. The patient assessment apparatus of claim 5, wherein the primary pivot connector includes indicia of angular rotation for indicating a rotation angle of the first or second extending portions.

10. The patient assessment apparatus of claim 1, wherein the first and second receiving members lie along different axes from each other with respect to a longitudinal axis of the elongated member.

11. The patient assessment apparatus of claim 1, wherein the first and third positions are equidistant from the second position.

12. The patient assessment apparatus of claim 1, wherein the elongated member includes a fourth position along the length of the elongated member adjacent the first position, and a fifth position along the length of the elongated member adjacent the third position, and further comprising a third receiving member situated at the fourth position, and a fourth receiving member situated at the fifth position.

13. The patient assessment apparatus of claim 12, wherein the fourth and fifth positions are equidistant from the second position.

14. The patient assessment apparatus of claim 12, further comprising at least one secondary pivot connector situated between the first and fourth positions or the second and fifth positions.

15. The patient assessment apparatus of claim 1, further comprising first and second markers.

16. The patient assessment apparatus of claim 1, wherein the arc member is rotatable with respect to the elongated member.

17. The patient assessment apparatus of claim 1, further comprising one or more objects slidably disposed on the arc member.

18. A patient assessment apparatus, comprising:
an elongated member having a length and first, second and third positions along the length;
an arc member attached to the elongated member;
a first receiving member situated at the first position;
a second receiving member situated at the third position, the second position situated between the first and third positions, the first and second receiving members each for receiving a marker from a patient for use in patient assessment;
a primary pivot connector situated at the second position, the elongated member including a first extending portion and a second extending portion extending from and rotatable about the primary pivot connector; and
a support member extending from the primary pivot connector and supporting the elongated member, wherein at least one of the elongated member and the support member are segmented so as to be modular for assembly and disassembly of the apparatus.

* * * * *